(12) United States Patent
Peretta et al.

(10) Patent No.: US 11,109,824 B2
(45) Date of Patent: Sep. 7, 2021

(54) MULTIMODAL SYSTEM FOR OBTAINING SENOLOGICAL IMAGES BY MEANS OF X-RAY AND MBI TECHNIQUES

(71) Applicant: METALTRONICA S.P.A, Pomezia (IT)

(72) Inventors: Giovanni B. Peretta, Pomezia (IT); Stefano Gioia, Pomezia (IT)

(73) Assignee: METALTRONICA S.P.A., Pomezia (IT)

( * ) Notice: Subject to any disclaimer, the term of this patent is extended or adjusted under 35 U.S.C. 154(b) by 0 days.

(21) Appl. No.: 16/759,302

(22) PCT Filed: Oct. 26, 2018

(86) PCT No.: PCT/IT2018/050210
§ 371 (c)(1),
(2) Date: Apr. 24, 2020

(87) PCT Pub. No.: WO2019/082225
PCT Pub. Date: May 2, 2019

(65) Prior Publication Data
US 2020/0297295 A1    Sep. 24, 2020

(30) Foreign Application Priority Data
Oct. 26, 2017    (IT) .......................... 102017000121925

(51) Int. Cl.
*A61B 6/00* (2006.01)
*A61B 6/04* (2006.01)

(52) U.S. Cl.
CPC .......... *A61B 6/4417* (2013.01); *A61B 6/0414* (2013.01); *A61B 6/4216* (2013.01);
(Continued)

(58) Field of Classification Search
CPC ... A61B 6/4417; A61B 6/0414; A61B 6/4216; A61B 6/4258; A61B 6/4291; A61B 6/502; A61B 6/4057; A61B 6/5247
See application file for complete search history.

(56) References Cited

U.S. PATENT DOCUMENTS 6,242,743 B1 *   6/2001   DeVito .................. A61B 6/037
                                                 250/363.01
2003/0194050 A1  10/2003  Eberhard et al.
(Continued)

OTHER PUBLICATIONS

Search Report dated Jun. 8, 2018 by the Italian Patent Office in connection with the prior Italian patent application.

*Primary Examiner* — Blake C Riddick
(74) *Attorney, Agent, or Firm* — Platinum Intellectual Property LLP

(57) ABSTRACT

The present invention relates to a multimodal system for obtaining senological images by means of X-ray and MBI techniques.
Said multimodal system comprises:
a supporting plane (1) for the breast,
a gamma ray detector (2A) for obtaining at least a molecular image,
a detection module (10) comprising inside said gamma ray detector (2A), where said gamma ray detector (2A) is arranged on a first plane, parallel to said supporting plane, as well as:
at least one between an X-ray detector (4) for obtaining at least an X-ray image and a scintigraphic collimator (2B); said scintigraphic collimator (2B), when in use, being coupled with said gamma ray detector (2A) and forming with said gamma ray detector (2A) a first gamma camera (2);
a compartment (3) configured for receiving one at time said X-ray detector (4) or said scintigraphic collima-
(Continued)

tor (2B), where said compartment (3) is arranged between said supporting plane (1) and said gamma ray detector (2A) on a second plane, parallel to said supporting plane (1), different from said first plane.

16 Claims, 15 Drawing Sheets

(52) U.S. Cl.
CPC .......... *A61B 6/4258* (2013.01); *A61B 6/4291* (2013.01); *A61B 6/502* (2013.01); *A61B 6/4057* (2013.01); *A61B 6/5247* (2013.01)

(56) References Cited

U.S. PATENT DOCUMENTS

| | | | |
|---|---|---|---|
| 2003/0197127 A1* | 10/2003 | Wainer | A61B 6/037 250/363.02 |
| 2007/0232881 A1* | 10/2007 | Shai | A61B 6/5235 600/407 |
| 2008/0061242 A1* | 3/2008 | Vija | A61B 6/4258 250/363.08 |
| 2008/0087833 A1* | 4/2008 | McCroskey | A61B 5/0059 250/370.08 |
| 2010/0260316 A1 | 10/2010 | Stein et al. | |
| 2010/0261997 A1* | 10/2010 | Ren | A61B 6/4411 600/424 |
| 2010/0329418 A1* | 12/2010 | Blevis | A61B 6/502 378/37 |
| 2011/0103544 A1* | 5/2011 | Hermony | A61B 6/037 378/19 |
| 2014/0093035 A1 | 4/2014 | Beekman | |
| 2014/0276032 A1* | 9/2014 | Majewski | A61B 6/0407 600/431 |
| 2015/0320375 A1* | 11/2015 | De Jong | A61B 6/4291 378/63 |
| 2019/0154845 A1* | 5/2019 | Holdsworth | G01T 1/161 |

* cited by examiner

MULTIMODAL SYSTEM FOR OBTAINING SENOLOGICAL IMAGES BY MEANS OF X-RAY AND MBI TECHNIQUES

RELATED APPLICATIONS

This application is a United States National Stage Application filed under 35 U.S.C 371 of PCT Patent Application Serial No. PCT/IT2018/050210, filed Oct. 26, 2018, which claims Italian Patent Application Serial No. IT102017000121925, filed Oct. 26, 2017, the disclosure of all of which are hereby incorporated by reference in their entirety.

The present invention relates to a multimodal system for obtaining senological images by means of X-ray and MBI (Molecular Breast Imaging) techniques.

More particularly, the present invention relates to the structure of a multimodal system comprising a detection module configured to allow the insertion of an X-ray detector or a scintigraphic collimator of a first gamma camera inside the same detection module in a predetermined position, i.e. between a breast supporting plane and a gamma ray detector being part of said first gamma camera, and allow, when it is necessary, the extraction of the X-ray detector from the detection module to insert the scintigraphic collimator or the extraction of the scintigraphic collimator to insert the X-ray detector.

A multimodal system is to be intended as a system for a breast diagnosis capable of detecting lesions by one or more images of the breast itself, which can be X-ray images, molecular images or images obtained by combining one or more X-ray images and one or more molecular images. Said images can also be used for breast biopsy.

The X-ray detector has a sensitive area capable of capturing X-rays and is configured to obtain at least a first image of the breast starting from the X-rays emitted by an X-ray unit which is part of the multimodal system, configured to emit X-rays and positioned in such a way that, when in use, said X-rays incide on said area, going through the breast.

The first gamma camera is configured to obtain one or more molecular images of the breast starting from the gamma rays emitted by a breast of a person, when the latter has taken a radioactive drug or radiopharmaceutical.

In particular, as already said, said first gamma camera comprises said gamma-ray detector and said scintigraphic collimator.

Said gamma ray detector includes:
- a scintillator crystal converting gamma rays into light radiations,
- a conversion device, connected to said scintillator crystal, wherein said conversion device has a sensitive area capable of capturing said light radiations and is configured to convert the information contained in said light radiations into at least a second image of the sine, depending on light radiation incident on said area.

Said scintigraphic collimator is provided with a matrix of holes for collimating said gamma rays on said scintillator crystal.

Moreover, said multimodal system comprises a processing device, connected to the X-ray detector and configured to receive and process said at least one first image (when said X-ray detector is inserted in the detection module), as well as connected to said gamma ray detector and configured to receive and process said at least one second image.

In particular, the processing device is configured to process said at least one first image in order to obtain at least one further first image or X-ray image used for the breast diagnosis and to process said at least one second image in order to obtain at least one further second image or molecular image used for the breast diagnosis.

Both the images obtained through the X-ray detector and the images obtained through the gamma-ray detector are called pre-processing images, and, starting from such pre-processing images, it is possible to obtain, through a processing of known type, respective further images, called post-processing images.

In particular, the pre-processing images are in a first format, for example in RAW format, and the post-processing images are in a second format, different from the first format, for example in DCM format.

Furthermore, in the context of multimodal systems, it is known that there are softwares to obtain a breast image as a combination of at least one X-ray image and at least one molecular image.

Said softwares also allow to obtain the spatial coordinates of a tumor lesion or a zone of suspect tissue, starting from X-ray images or molecular images or a combination of such images.

PRIOR ART

Currently, several multimodal systems are known.

An example of a multimodal system of a known type is described in the international application WO 2010/120658.

Said multimodal system of a known type comprises a breast supporting plane, a digital detector and a gamma camera, arranged between said supporting plane and said digital detector.

Furthermore, an anti-diffusion grid for reducing X-ray diffusion is arranged above said digital detector, between said digital detector and said gamma camera.

The digital detector is an X-ray detector and can move laterally or rotate around one or more points and its movement can be controlled by a control motor.

The gamma camera is movable within the system between a first position, in which the gamma camera is above the anti-diffusion grid, and a second position, in which the gamma camera is translated along a horizontal axis and is no longer above the anti-diffusion grid. The movement of said gamma camera can be motorized or manual.

The anti-diffusion grid is movable within said system between a first position, wherein said anti-diffusion grid is above said digital detector, and a second position, wherein said anti-diffusion grid is translated along a further horizontal axis, parallel to said first horizontal axis, and is no longer above said digital detector.

However, a disadvantage of said multimodal system of a known type is given by the fact that the quality of the image obtained by X-ray is reduced because it depends on a predetermined distance between the supporting plane for the breast and the digital detector (i.e. X-ray detector).

Consequently, one or more specific processing on the pre-processing images and/or post-processing images (i.e. images obtained via the X-ray detector) are necessary to take into account for such a predetermined distance.

Such a predetermined distance remains, although during mammography both the anti-diffusion grid and the gamma camera are moved to the respective second position.

AIM OF THE INVENTION

The aim of the present invention is to overcome said disadvantage by providing a multimodal system for obtaining senological images by X-ray and MBI techniques, whose structure is designed to obtain at least a good quality X-ray image, without the need that the latter is subjected to one or more further processing on the pre-processing images and/or post-processing images.

This was achieved by means of a multimodal system comprising a breast supporting plane and a detection module comprising in turn a gamma ray detector of a first gamma camera, where said gamma ray detector is in a fixed position inside of said detection module or mobile on a plane, parallel to said breast supporting plane, and said detection module comprises a compartment configured to receive one at time an X-ray detector or a scintigraphic collimator of said first camera range, in a position between said gamma ray detector and said breast supporting plane.

A further object of the invention is to provide a multimodal system, the structure of which is simple and cheap, since there are no mechanical and/or electronic moving means for moving the X-ray detector inside the detection module.

OBJECT OF THE INVENTION

It is therefore object of the invention a multimodal system for obtaining senological images by means of X-ray and MBI techniques, comprising
 a supporting plane for the breast,
 a gamma ray detector for obtaining at least a molecular image,
 a detection module comprising inside said gamma ray detector, where said gamma ray detector is arranged on a first plane, parallel to said supporting plane, as well as:
  at least one between an X-ray detector for obtaining at least an X-ray image and a scintigraphic collimator, where said scintigraphic collimator, when in use, is coupled with said gamma ray detector and forms with said gamma ray detector a first gamma camera;
  a compartment configured for receiving one at time said X-ray detector or said scintigraphic collimator, where said compartment is arranged between said supporting plane and said gamma ray detector on a second plane, parallel to said supporting plane, different from said first plane.

In particular, said compartment can comprise first guiding means for inserting said X-ray detector or said scintigraphic collimator.

More particularly, said first guiding means can comprise a first guiding element, arranged on a first side of said compartment, and a second guiding element, arranged on a second side of said compartment, opposite said first side.

Said detection module can comprise said supporting plane and said supporting plane can be a first surface of said detection module or said supporting plane can be coupled with a first surface of said detection module in a removable manner.

With particular reference to the X ray detector, said X ray detector can comprise inside an anti-diffusion grid.

Furthermore, said X-ray detector can comprise first moving means for moving said anti-diffusion grid along an axis lying on a third plane parallel to said supporting plane, where said first moving means can be manual or motorized.

With particular reference to the gamma camera detector, said gamma ray detector can be arranged in a fixed position or movable on said first plane.

In an alternative, said gamma ray detector and said scintigraphic collimator can have dimensions equal to each other and smaller than the dimensions of said compartment, and said first gamma camera can be movable on said first plane.

In particular, said first gamma camera can be configured to translate along a first axis, and along a second axis, perpendicular to said first axis, where said first axis and said second axis lie on said first plane.

Furthermore, said detection module can comprise inside second moving means for moving said first gamma camera along said first axis and said second axis, where said second moving means are connected to said gamma ray detector; where said second moving means can be manual or motorized.

According to the invention, said multimodal system can comprise:
 a body,
 an arm, connected to said body in such a way as to rotate with respect to said body of a predetermined angle, and
 a second gamma camera,
 supporting and connecting means for supporting said second gamma camera and connecting said second gamma camera to said arm in such a way that said second gamma camera is movable along a third axis, perpendicular to said support plane, where said supporting and connecting means comprising:
  a first element, connected to said second gamma camera, and
  a second element connected to said first element, as well as to said arm so as to slide along said third axis.

Said first element is rotatably connected to said second element so as to rotate around a fourth axis, perpendicular to said supporting plane, and said second gamma camera is connected to said first element so as to rotate in the space around a point.

With reference to the second gamma camera, said second gamma camera can be connected to said first element by means of a spherical joint.

Furthermore, said second gamma camera can comprise rotating means for rotating said second gamma camera around said spherical joint, where said rotating means can be manual or motorized.

Advantageously, said first element comprises a first surface and said second gamma camera can slide on said first surface along a fifth axis, perpendicular to said third axis.

In particular, said first surface can be provided with third guiding means to allow the sliding of the second gamma camera along said first surface.

Furthermore according to the invention, said multimodal system can comprise a compressor, coupable to said second element, where said compressor is provided with an opening to allow said second gamma camera to contact a breast portion at said opening, and said second element can be provided with coupling means to allow said compressor to be coupled with said second element in a removable manner.

Furthermore, said multimodal system can comprise third moving means for moving said second gamma camera along said first surface, where said third moving means can be manual or motorized, and fourth moving means for rotating said first element with respect to said second element, where said fourth moving means are manual or motorized.

LIST OF FIGURES

The present invention will be now described, for illustrative, but not limitative purposes, according to its embodiment, making particular reference to the enclosed figures, wherein.

DETAILED DESCRIPTION OF THE INVENTION

Figure 1A:
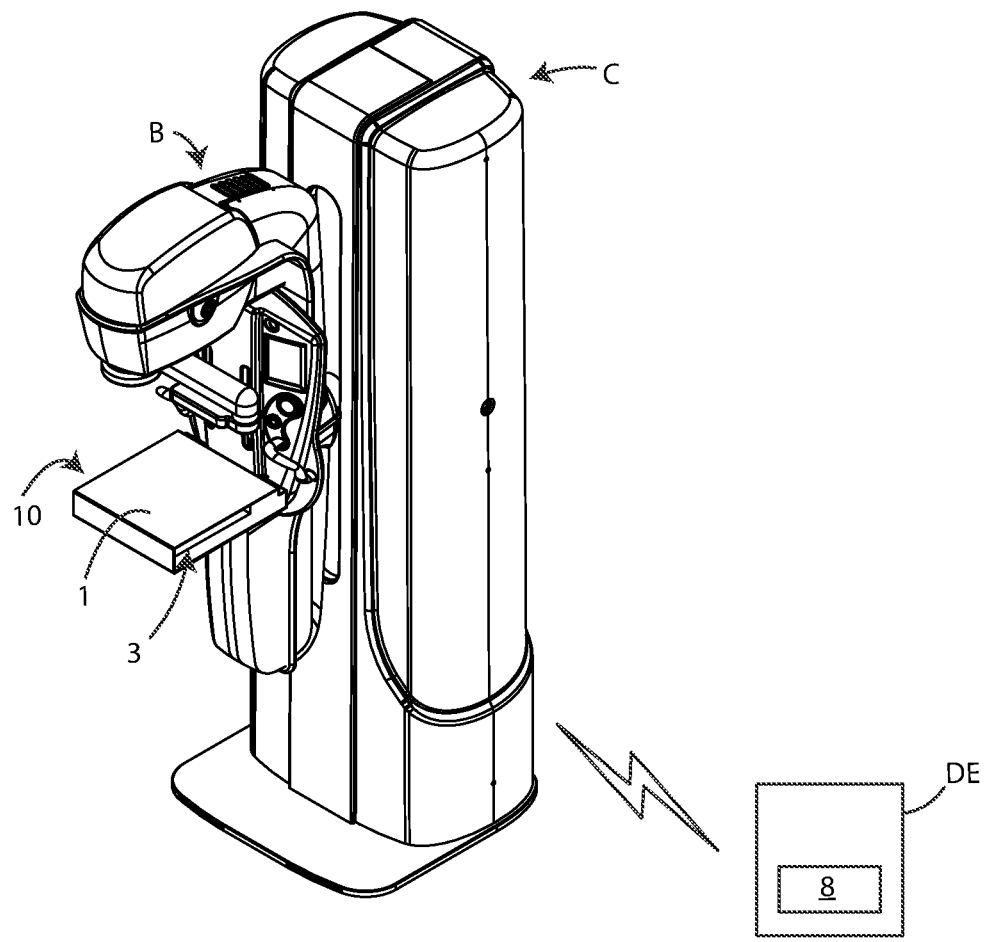
FIG. 1A is a perspective view of the multimodal system, object of the invention, in which inside the detection module there is neither an X-ray detector nor a scintigraphic collimator.
Figure 1B:
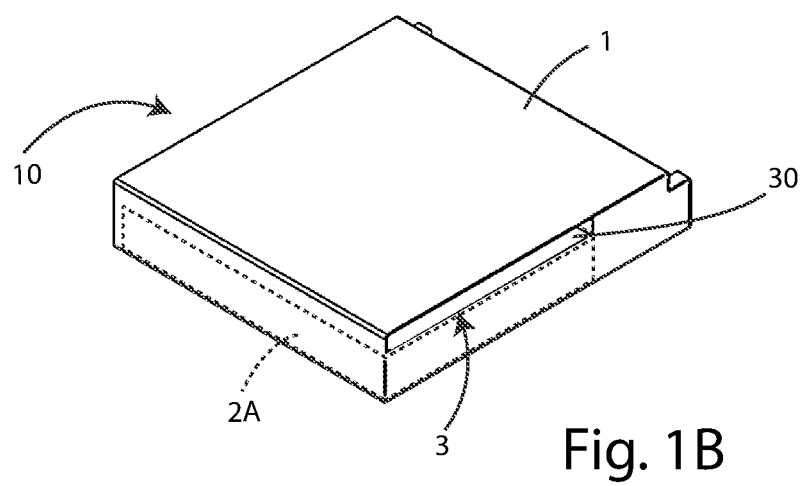
FIG. 1B is a schematic view of the detection module of the multimodal system of FIG. 1A.

With particular reference to FIGS. 1A, 1B a multimodal system for obtaining senological images by means of X-ray and MBI techniques.

Said multimodal system comprises:
- a body C comprising a high voltage generator and the related control unit,
- an arm B, connected to said body C in such a way as to rotate with respect to said body C of a predetermined angle, provided with a X ray tube (not shown) for generating X rays, connected to said high voltage generator and powered by the latter,
- a supporting plane 1 for the breast (i.e. to allow the breast of a person to be positioned), preferable made of carbon fiber,
- a gamma ray detector 2A being part of a first gamma camera 2 for obtaining at least a molecular image,
- a detection module 10 comprising inside said gamma ray detector 2A, where said gamma ray detector 2A is arranged on a first plane, parallel to said supporting plane, as well as:
  - at least one between an X-ray detector for obtaining at least an X-ray image, indicated with the reference number 4, or a scintigraphic collimator 2B, being part of said first gamma camera 2;
  - a compartment 3 configured for receiving one at time said X-ray detector 4 or said scintigraphic collimator 2B, where said compartment 3 is arranged between said supporting plane 1 and said gamma ray detector 2A, on a second plane, parallel to said supporting plane, different from said first plane.

In other words, the system can comprise an X ray detector 4 or a scintigraphic collimator 2B or both (although when the multimodal system is in use, only one between the X ray detector and the scintigraphic collimator is used) and the compartment 3 is conceived to receive in turn the X ray detector 4 and the scintigraphic collimator 2B, depending on the type of the senological image to be obtained, in such a way that:

when the X ray detector 4 is received by the compartment 3, said compartment is occupied by said X ray detector 4 and the presence of said scintigraphic collimator 2B inside said compartment 3 is excluded, when the scintigraphic collimator 2B is received by the compartment 3, said compartment 3 is occupied by said scintigraphic collimator 2B and the presence of said X ray detector 4 inside said compartment is excluded.

In fact, when the X ray detector 4 is received by the compartment 3, said X ray detector 4 is arranged between the supporting plane 1 and the gamma ray detector 2A (the scintigraphic collimator 2B will not be present in the compartment 3) in such a way as to be in contact or substantially in contact with the supporting plane 1, and it is possible to obtain a senological image by means X ray technique.

When the scintigraphic collimator 2B is received by the compartment 3, said scintigraphic collimator 2B is arranged between the supporting plane 1 and the gamma ray detector 2A (the X ray detector will not be present in the compartment 3) in such a way as to be in contact with the gamma ray detector 2A, and it is possible to obtain a senological image by means MBI technique. In this specific case, the gamma ray detector 2A and the scintigraphic collimator 2B (arranged in the same compartment) form the first gamma camera 2.

Hence, in the event of the multimodal system comprises either the X ray detector 4 and the scintigraphic collimator 2B, the use of the X ray detector is alternative to the use of the scintigraphic collimator and vice versa.

Consequently, the compartment 3, which occupies a fixed position with respect to the supporting plane 1 (i.e. the compartment 3 is not movable inside the detection module with respect the supporting plane 1), is adapted to receive the X ray detector X and the scintigraphic collimator 2B only one at time, so that the distance between the X ray detector 4 (when said X ray detector is inserted in the compartment 3) and the supporting plane 1 is equal to the distance between the gamma camera 2 (when the scintigraphic collimator 2B is inserted in the compartment 3) and the supporting plane 1.

The compartment 3 is positioned below the supporting plane 1 and therefore the distance of the X ray detector 4 or the gamma camera 2 is extremely reduced.

In the embodiment being disclosed, said detection module 10 comprises said supporting plane 1. In particular, said supporting plane 1 is a first surface of said detection module 10.

The gamma ray detector 2A is arranged on a second surface of said detection module 10, opposite to said first surface.

However, it is not necessary that said detection module 10 comprises said supporting plane 1.

In fact, said supporting plane 1 can be coupled with a first surface of said detection module 10 through coupling means of known type.

Furthermore, in the embodiment being disclosed, said gamma ray detector 2A is arranged in a fixed position inside said detection module 10.

Figure 2A:
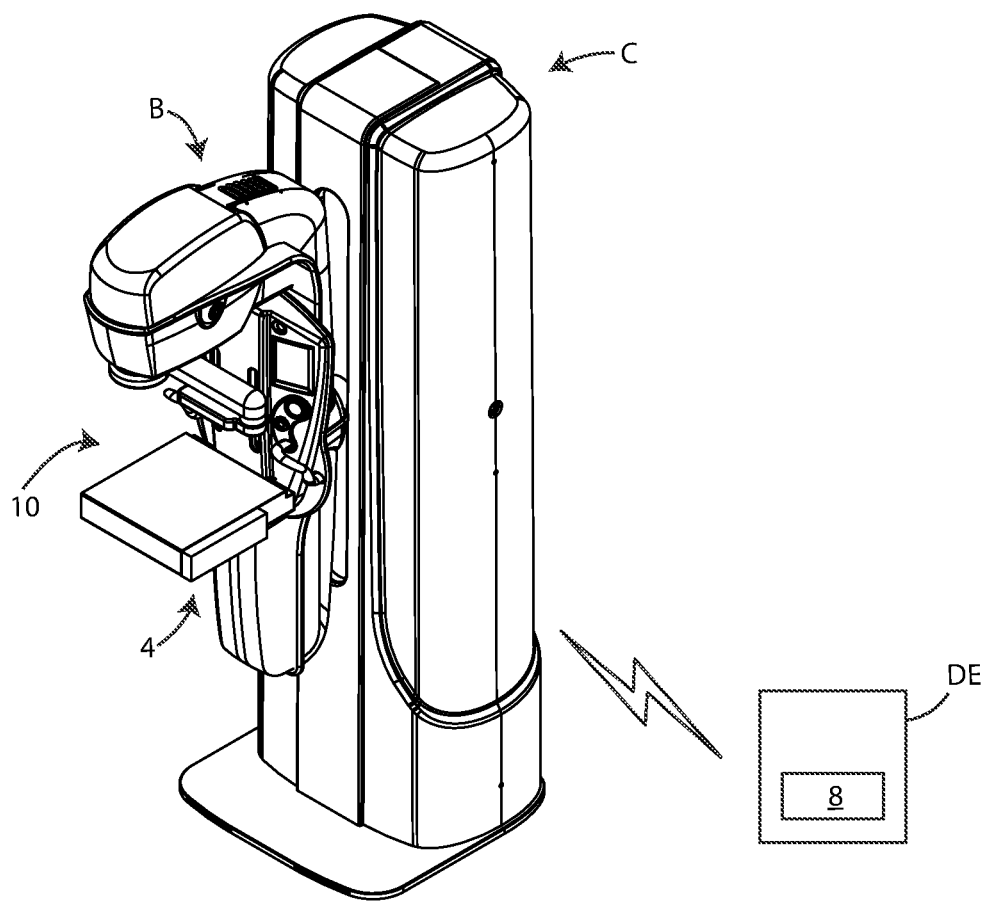
FIG. 2A is a perspective view of the multimodal system, object of the invention, in which an X-ray detector is arranged inside the detection module.

FIG. 2A shows the multimodal system when the X ray detector 4 is inserted in the compartment 3 of the detection module 10.

Hence, the X ray detector 4 is arranged between said gamma ray detector 2A and said supporting plane 1 and the multimodal system is used for obtaining one or more X ray images.

Figure 2B:
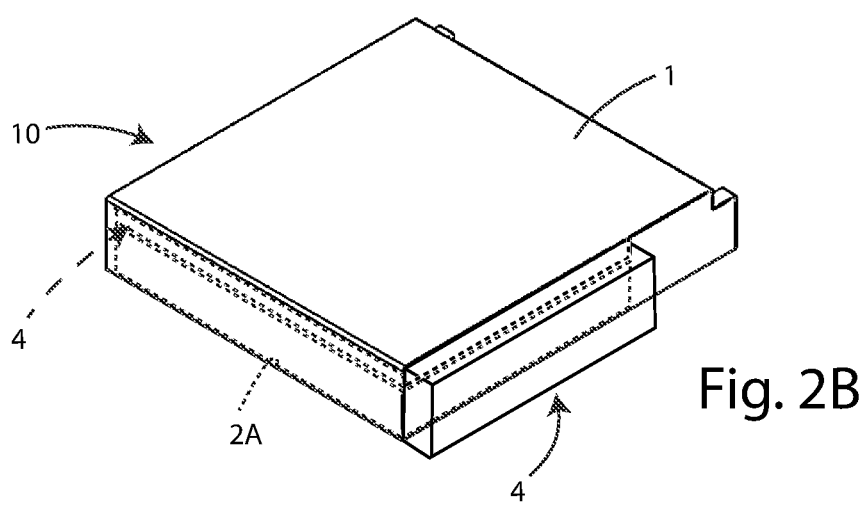
FIG. 2B is a schematic view of the detection module of the multimodal system of FIG. 2A, inside which the X-ray detector is arranged.

FIG. 2B is a schematic view of the detection module inside of which the X ray detector 4 is inserted.

Figure 2C:
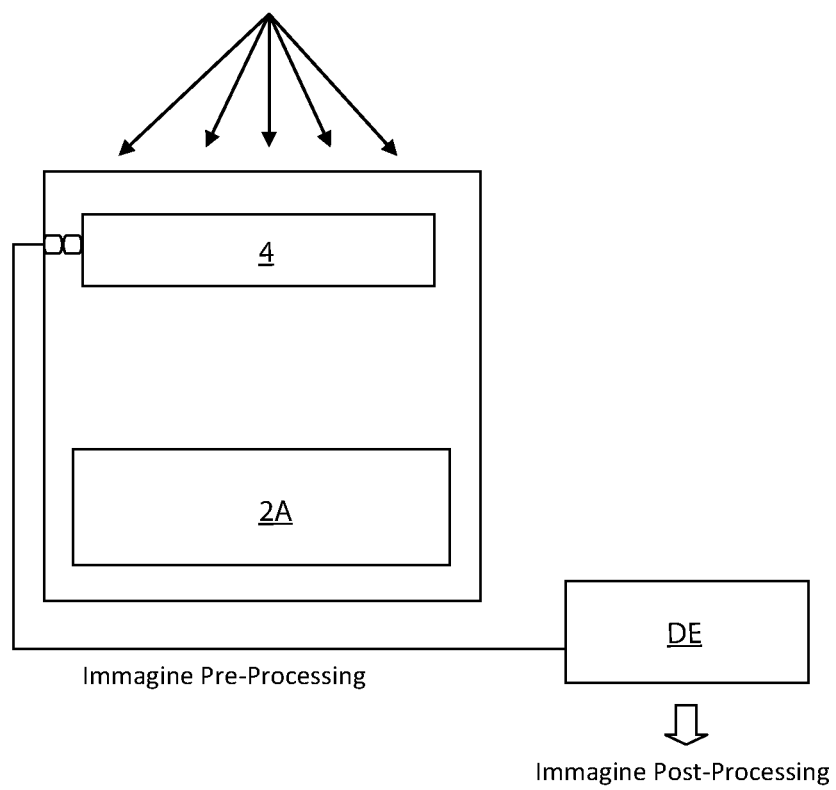
FIG. 2C shows the operating principle for obtaining an X-ray image used for breast diagnosis.

FIG. 2C shows the operating principle for obtaining an X ray image used for the breast diagnosis.

As it can be seen from the Figure, the X ray detector 4 captures X rays (emitted by the X rays unit through said X ray tube, not shown in FIG. 2C), indicated as arrows in Figure, by means of its sensitive area and generates at least a first image or pre-processing image, which is processed by a processing device DE, connected to said X ray detector, for obtaining a further first image or post-processing image.

In the embodiment being disclosed, said processing device DE is outside the body C of the multimodal system.

However, said processing device DE can be arranged inside said body C of the multimodal system.

Figure 3:
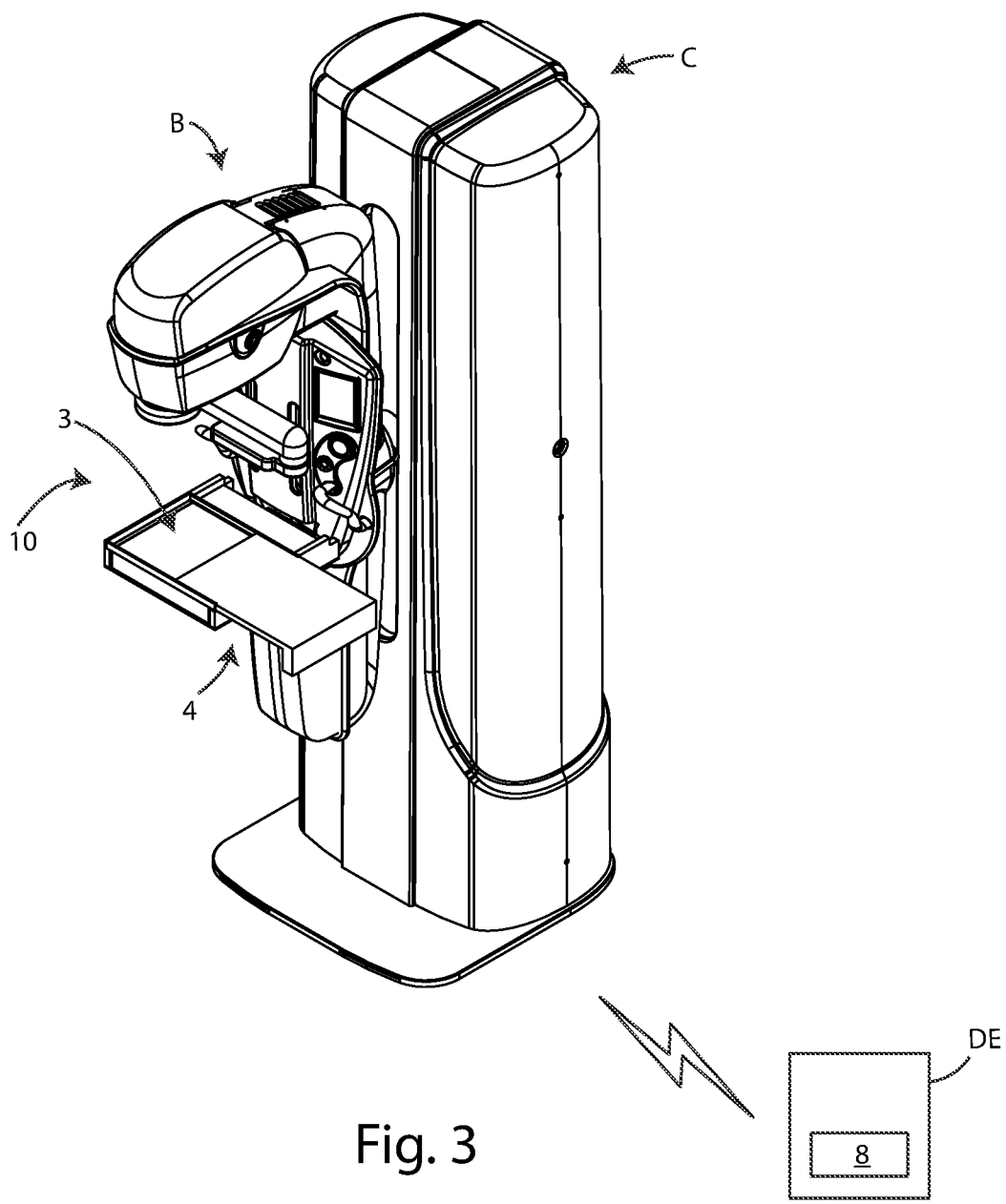
FIG. 3 shows the multimodal system of FIG. 1A without a supporting plane, in which the X-ray detector is partially extracted from the detection module.

FIG. 3 shows the detection module 10, when the X ray detector 4 is partially extracted by the compartment 3 of the detection module itself.

Figure 4A:
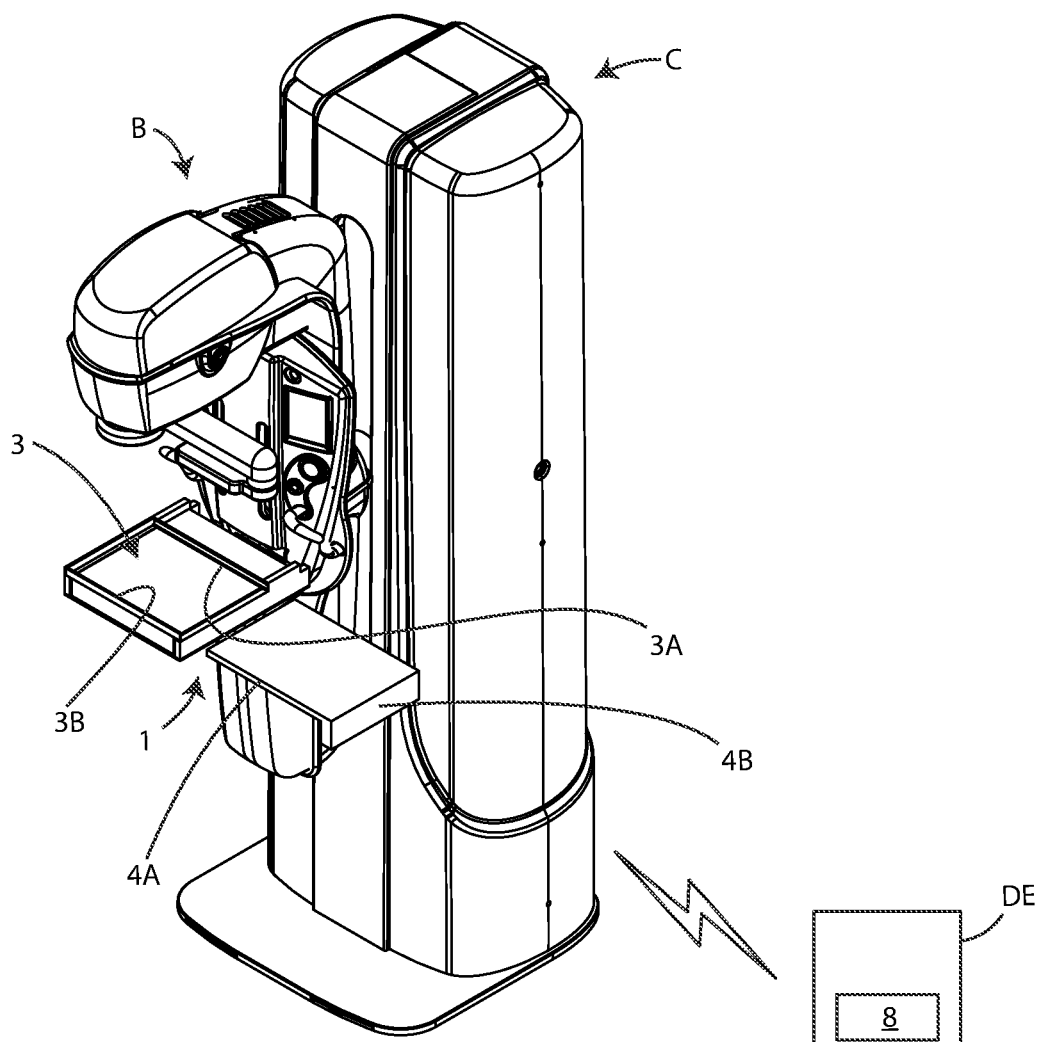
FIG. 4A shows the multimodal system of FIG. 1A the detection module of which has no supporting plane and the X-ray detector has been extracted from the detection module itself.

FIG. 4A shows the detection module when the X ray detector is extracted by the compartment 3 of the detection module itself.

Figure 4B:
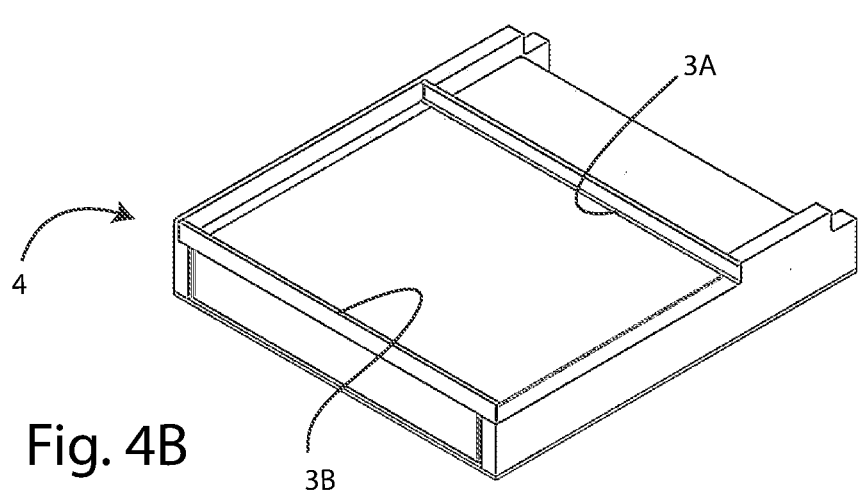
FIG. 4B shows the detection module without a supporting plane.

FIG. 4B shows the compartment 3 of the detection module 10 without supporting plane 1.

Said compartment 3 has an opening 30 to allow the insertion of the X ray detector 4 (or the scintigraphic collimator 2B) and is provided of first guiding means to allow said X ray detector 4 (or said scintigraphic collimator 2B) to slide inside said compartment 3.

Said first guiding means comprise a first guiding element 3A, arranged on a first side of said compartment 3, and a second guiding element 3B, arranged on a second side, opposite to said first side.

In the embodiment being disclosed, each guiding element is C-shaped.

It is sufficient to insert the X ray detector in the compartment 3 through the opening 30 and slide the X ray detector 4 on said first guiding means to position said X ray detector inside the compartment 3 in such a way that, when said X ray detector is inside said compartment 3, it is arranged between said supporting plane 1 and said gamma ray detector 2A.

Figure 5:
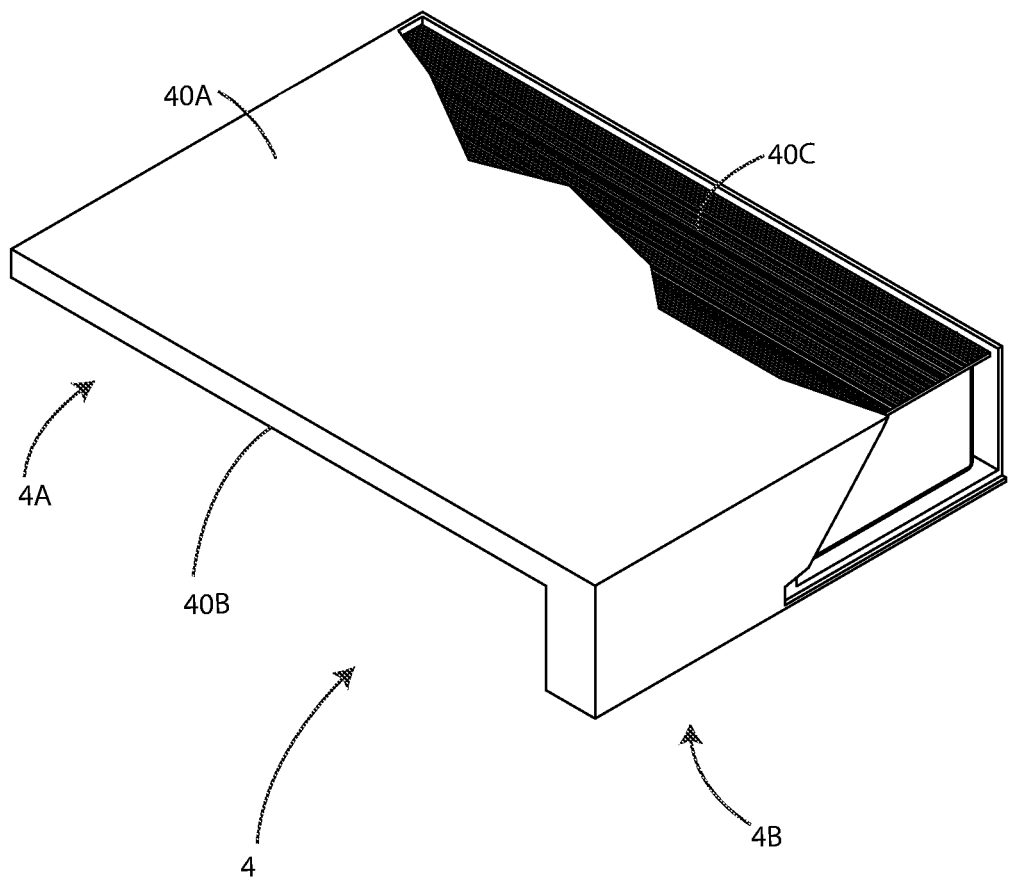
FIG. 5 shows the X-ray detector, from which a portion has been removed to make visible a portion of anti-diffusion grid, arranged inside the X-ray detector itself.

FIG. 5 shows the X ray detector 4.

Said X ray detector comprises at least a first part with shape and dimensions such as to be received in the compartment 3.

In the embodiment being disclosed, the X ray detector 4 is L-shaped and comprises a first part 4A shaped and dimensioned in such a way as to be received in the compartment 3, and a second part 4B, perpendicular to said first part 4A, intended to contact a portion of said detection module 10. In alternative, when said X ray detector is in use, said second part 4B can be at a predetermined distance form a portion of said detection module 10.

However, said X ray detector 4 can have any shape and dimensions provided that they are consistent with the shape and dimensions of the compartment, without departing from the scope of the invention.

Furthermore, in the embodiment being disclosed, said X ray detector 4 comprises inside an anti-diffusion grid 40C, arranged in such a way that, when said X ray detector is in use, said anti-diffusion grid 40C is arranged on a third plane, parallel to the supporting plane 1.

However, it is not necessary that said X ray detector 4 comprises inside said anti-diffusion grid.

In particular, the first part 4A of said X ray detector 4 comprises a first surface 40A and a second surface 40B, opposite to said first surface 40A, and said anti-diffusion grid 40C is arranged between said first surface 40A and a said second surface 40B, at a predetermined distance from said first surface 40A.

The sensitive area configured to capture X ray of said X ray detector is substantially equal to said first surface 40A.

In the embodiment being disclosed, said anti-diffusion grid 40C has dimensions substantially equal to the dimensions of the sensitive area of the X ray detector 4.

In an alternative (not shown in Figures), said anti-diffusion grid 40C can have dimensions greater than the dimensions of the sensitive area of the X ray detector 4 and said X ray detector 4 can comprise first moving means, connected to said anti-diffusion grid, for moving said anti-diffusion grid 40C along an axis placed on said third plane (which is coincident with a plane parallel to said first surface 40A), so that said anti-diffusion grid moves in a first direction or in a second direction, opposite to said first direction.

Said multimodal system comprises a control logic unit 8 which is connected to said first moving means and is configured to control said first moving means.

In the embodiment being disclosed, said control logic unit 8 is arranged inside the processing device DE.

However, said control logic unit 8 can be arranged elsewhere in the multimodal system, also outside the processing device DE.

The dimensions of the anti-diffusion grid greater than the dimensions of the sensitive area of the X ray detector 4 ensure that, during the movement of the anti-diffusion grid 40C, the projection of said sensitive area of the X ray detector 4 on said anti-diffusion grid 40C along an axis perpendicular to the supporting plane 1 falls always on said anti-diffusion grid.

Said first moving means can be electromechanical moving means, such a linear actuator.

In the embodiment being disclosed, said first moving means are motorized. However, said first moving means can be manual, without for this reason departing from the Invention.

However, the presence of an anti-diffusion grid inside the X ray detector 4 is not necessary.

Hence, the X ray detector 4 can be without the anti-diffusion grid 40C.

Figure 6A:
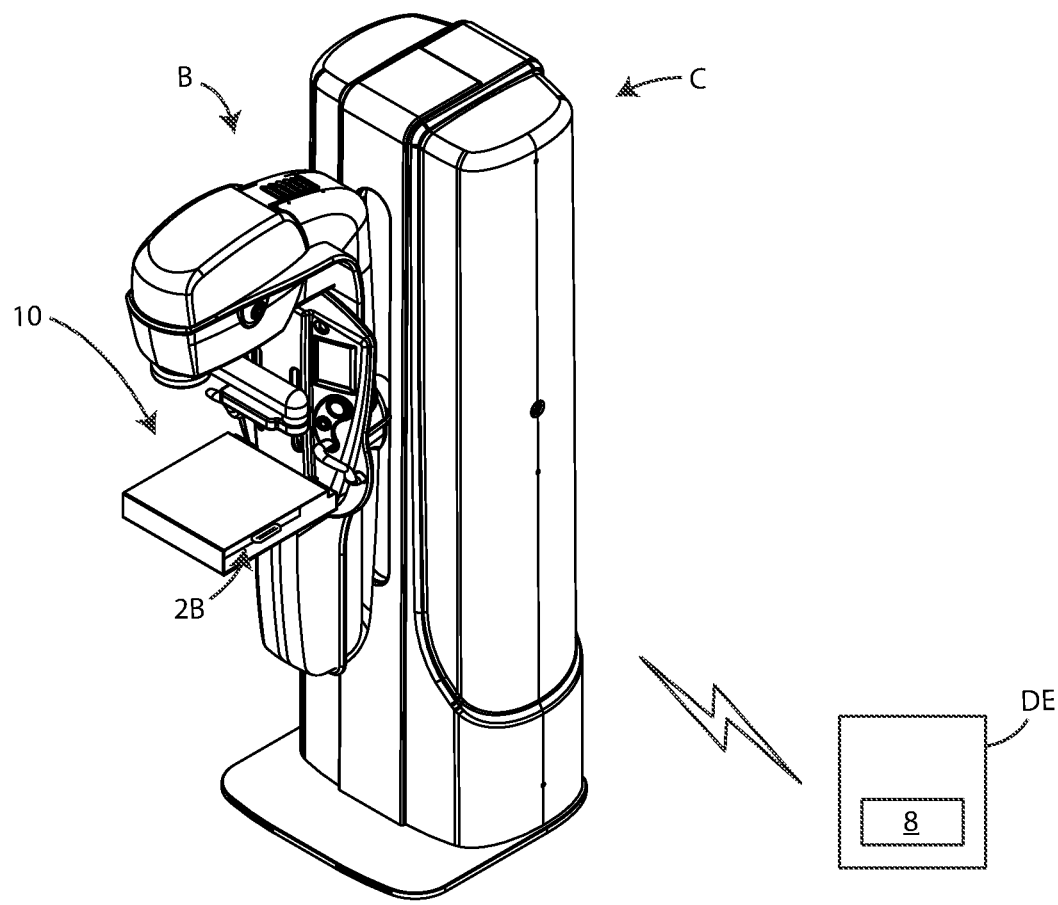
FIG. 6A is a perspective view of the multimodal system, object of the invention, in which a scintigraphic collimator is arranged within the detection module.

FIG. 6A shows the multimodal system when a scintigraphic collimator 2B is arranged inside the detection module 10.

This means that a possible X ray detector, arranged inside the compartment 3 of the detection module 10, has been extracted from the compartment 3 and replaced by the scintigraphic collimator 2B.

Hence, the scintigraphic collimator 2B is arranged between said gamma ray detector 2A and said supporting plane 1 and the multimodal system is used to obtain one or more molecular images of the breast.

The same compartment 3 of the detection module 10 is configured to receive said scintigraphic collimator 2B.

Figure 6B:
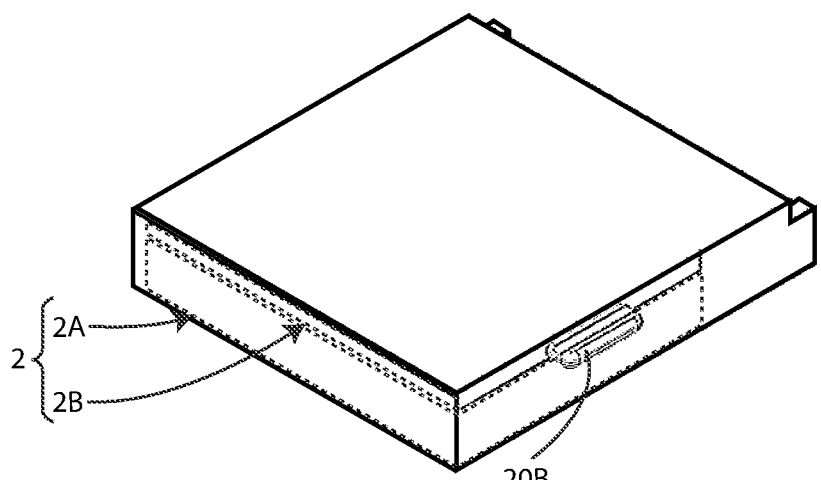
FIG. 6B is a schematic view of the detection module inside which the scintigraphic collimator is arranged.

FIG. 6B is a schematic view of the detection module 10, when a scintigraphic collimator 2B has been inserted in the compartment 3 of the detection module 10 and is coupled with said gamma ray detector 2A, so that said first gamma camera 2 is formed inside the detection module 10.

Said first gamma camera 2 comprises said gamma ray detector 2A and said scintigraphic collimator 2B.

Said gamma ray detector 2A comprises:
- a scintillator crystal for converting gamma rays into light radiations,
- a conversion device, connected to said scintillator crystal, for converting information contained in said light radiations in an image depending of the light radiation incident on a sensitive area of said conversion system, wherein said conversion is coupled with said scintillator crystal.

Said scintigraphic collimator 2B serves to collimate gamma ray on said scintillator crystal.

The gamma ray detector 2A is provided of a sensitive area for capturing gamma rays coming from the breast of a person (after that the latter took a radioactive drug) and said scintigraphic collimator 2B is provided of a matrix of holes to collimate said gamma rays toward to said sensitive area.

The holes of said matrix can be parallel or inclined.

Advantageously, when said holes are inclined, it is possible to obtain information on the breast tissue with reference to a zone of the breast itself, which it would not be possible to obtain with a matrix of parallel holes.

As it can be seen from FIG. 6B, said scintigraphic collimator 2B is arranged inside said compartment 3 in such a way as to be overlapped on said gamma ray detector 2A.

With reference to the position of the scintigraphic collimator 2B, it is arranged between said gamma ray detector 2A and said supporting plane 1.

In the embodiment being disclosed, said scintigraphic collimator 2B has a handle 20B to facilitate the grip of the same scintigraphic collimator and its use.

Figure 6C:
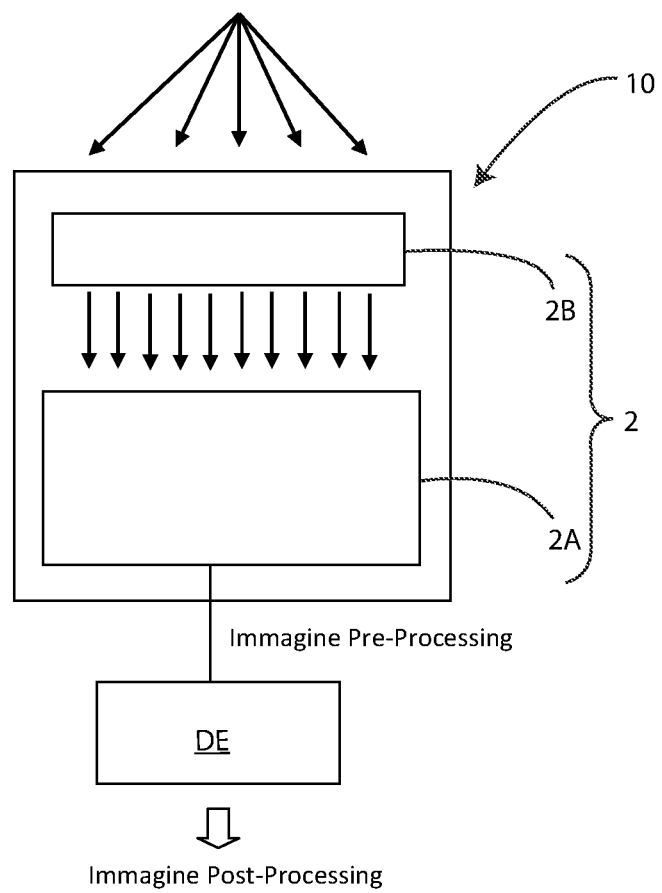
FIG. 6C shows the operating principle for obtaining a molecular image used for breast diagnosis.

FIG. 6C shows the operating principle to obtain a molecular image used for the breast diagnosis.

As it can be seen, the scintigraphic collimator 2B collimate the gamma rays, indicated as arrows in Figure, which are emitted by the breast (when a person took a radioactive drug) toward to the sensitive area of the gamma ray detector 2A and the latter generates at least a second image or preprocessing image, which is processed by the processing device DE, connected to said gamma ray detector 2A for obtaining a further second image or post-processing image.

Similarly to the X ray detector 4, also the scintigraphic collimator 2B is slid on said first guiding means of the compartment 3 inside the detection module 10.

Hence, said first guiding means, which allow the X ray detector 4 to slide inside the compartment 3 of the detection module 10, allow also the scintigraphic collimator 2B to slide inside the same compartment.

Figure 7:
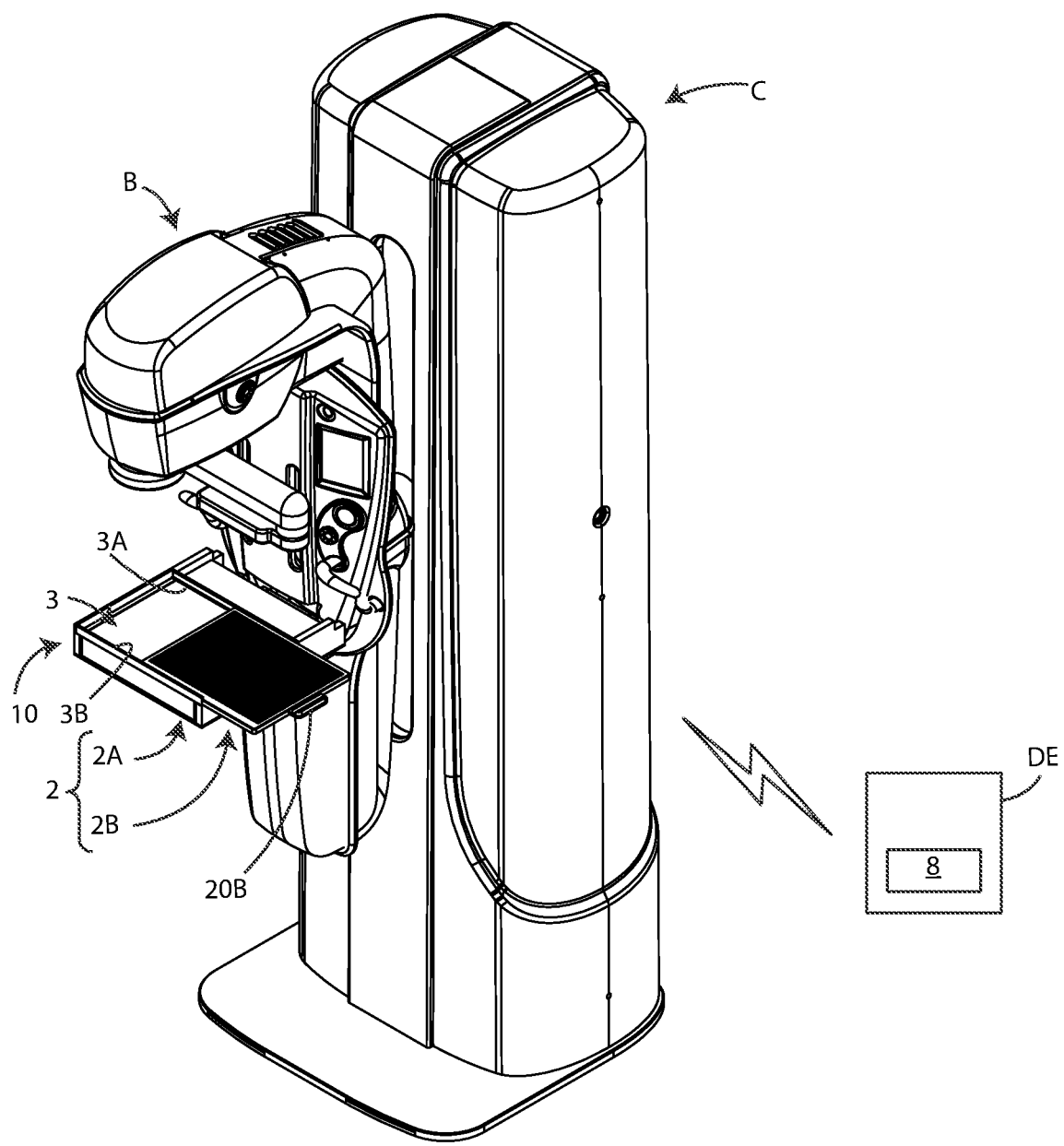
FIG. 7 shows the multimodal system of FIG. 6A without a supporting plane for the breast, in which the scintigraphic collimator is partially extracted from the detection module.

FIG. 7 shows the scintigraphic collimator 2B partially extracted from the compartment 3 of the detection module 10.

Figure 8:
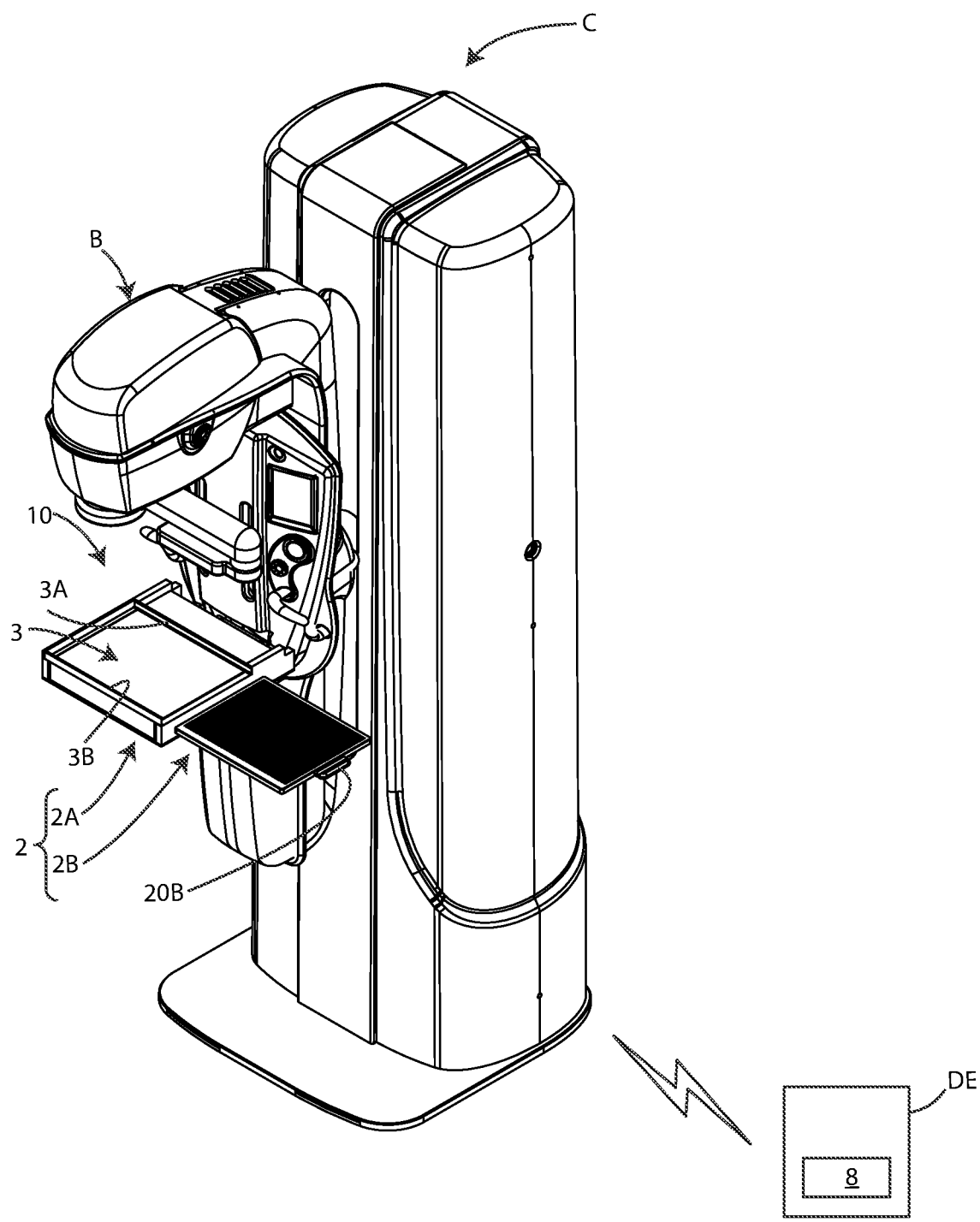
FIG. 8 shows the multimodal system of FIG. 6A without a supporting plane, in which the scintigraphic collimator has been extracted from the detection module.

FIG. 8 shows the scintigraphic collimator 2B extracted from the compartment 3 of the detection module 10.

In the embodiment being disclosed, the sensitive area of the X ray detector 4 has dimensions equal to the dimensions of the sensitive area of the gamma ray detector.

However, it is not necessary that the dimensions of the sensitive area of the gamma ray detector are equal to the dimensions of the sensitive area of the X ray detector 4.

Figure 9A:
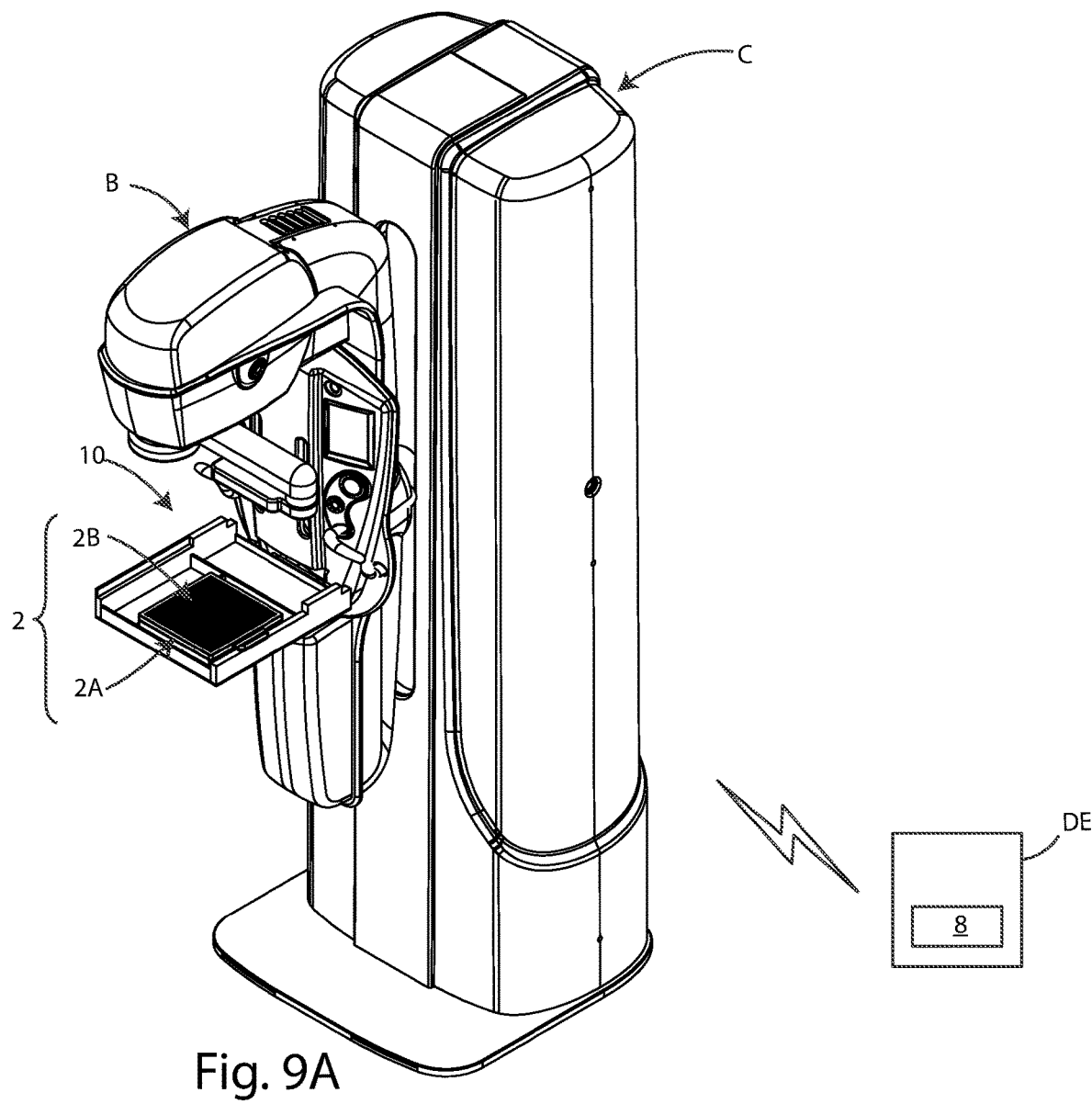
FIG. 9A shows a variant of the multimodal system of FIG. 6A in which the supporting plane for the breast has been removed to show the gamma-ray detector and the scintigraphic collimator coupled together in such a way as to form a first gamma camera, wherein said first gamma camera is in a first position inside the detection module.
Figure 9B:
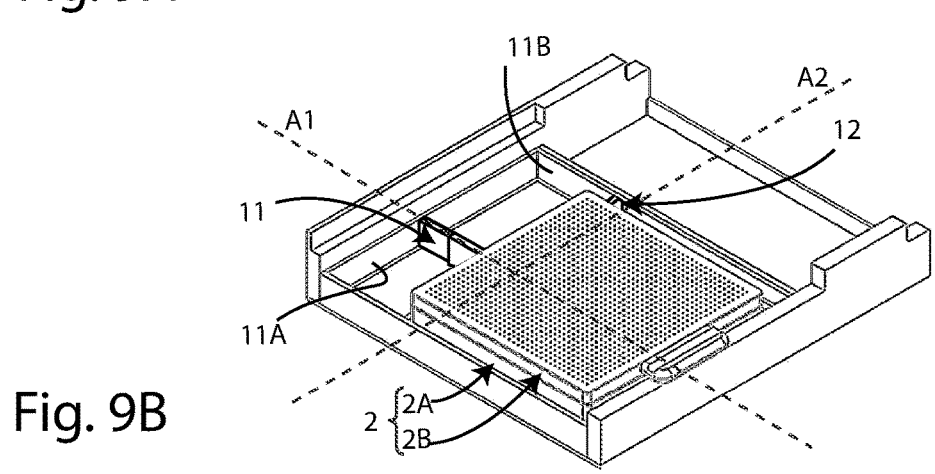
FIG. 9B shows a detail concerning the first gamma camera arranged inside the detection module.
Figure 10:
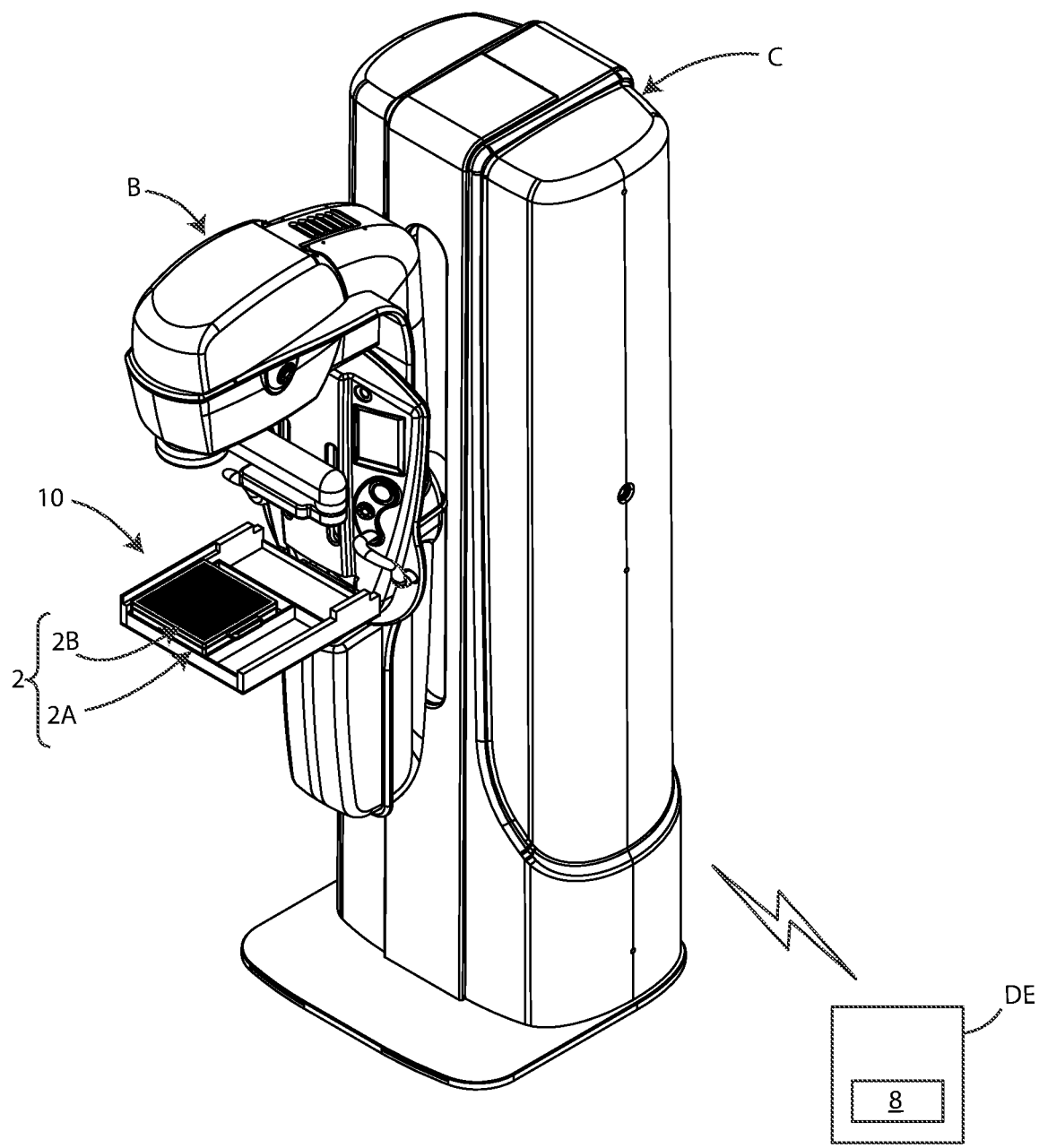
FIG. 10 shows the variant of the multimodal system of FIG. 9, wherein said first gamma camera is in a second position inside the detection module.

For example, in a variant, shown in FIGS. 9A, 9B and 10, the dimensions of the sensitive area of the gamma ray detector 2A are smaller than the dimensions of the sensitive area of said gamma X ray detector, FIG. 9A shows a variant of the multimodal system (without supporting plane) in which the first gamma camera 2 comprises the gamma ray detector 2A and the scintigraphic collimator 2B coupled to each other through coupling means of known types.

For example, said coupling means of known can be snap coupling means.

In such a variant, said gamma ray detector 2A has dimensions equal to the dimensions of the scintigraphic collimator 2B, and both have dimensions less than the dimensions of the compartment 3 of the detection module 10.

As it can be seen from the FIG. 9B, said first gamma camera 2 is configured to translate along a first axis A1 (parallel to said first guiding means), and along a second axis A2, perpendicular to said first plane A1, where bot of the axis lie on said first plane.

Said first gamma camera 2 is configured to move inside the detection module 10 starting from a first position, in proximity of the opening 30 of the compartment 10, and a second position, in which it is translated along said first axis A1 and/or along said second axis A2, vice and versa.

FIG. 9A shows the first gamma camera 2 in said first position inside the detection module.

FIG. 10 shows the first gamma camera 2 in a second position, in which said first gamma camera 2 is translated along said first axis.

The movement of said first gamma camera can be manual ore motorized.

In the embodiment being disclosed, said movement is motorized

Said detection module 10 comprises inside second moving means (not shown) to move said first gamma camera 2, connected to said ray gamma detector 2A.

In the embodiment being disclosed, said second moving means are motorized. However, said second moving means can be manual, without for this reason departing from the invention.

For example, as it can be seen in FIG. 9B, said second moving means can comprise a first linear actuator, preferable a precision linear actuator, to move said first gamma camera 2 along said first axis A1, and a second linear actuator, preferable a precision linear actuator, to move said first gamma camera 2 along said second axis A2.

Said first actuator comprises a first arm 11, where said first arm comprises a first part and a second part, sliding inside said first part, where said first arm 11 is connected to said gamma ray detector 2A and a first wall of the detection module 10 in such a way as to slide along said first wall through guiding means 11A.

Said second actuator comprises a second arm 12, where said second arm comprises a first part and a second part, sliding inside said first part, where said second arm is connected to said gamma ray detector 2A and a second wall of the detection module 10, perpendicular to said first wall, in such a way as to slide along said wall through further guiding means 11B.

In the embodiment being disclosed, said moving means 11A and said further guiding means 11B comprise respectively a third guiding element C-shaped and a fourth guiding element C-shaped.

In other words, said second moving means allow said gamma ray detector 2A to slide along said first axis A1 and/or said second axis A2 and to be positioned in said first position, in proximity of the opening 30 of said compartment 3 of the detection module 10, either to allow the scintigraphic collimator 2B to be inserted and coupled with the gamma ray detector 2A, and to allow the scintigraphic collimator 2B to be manually extracted, after its use.

Furthermore, said control logic unity 8 is connected to said second moving means and is configured to send a position signal to said moving means.

Figure 11:
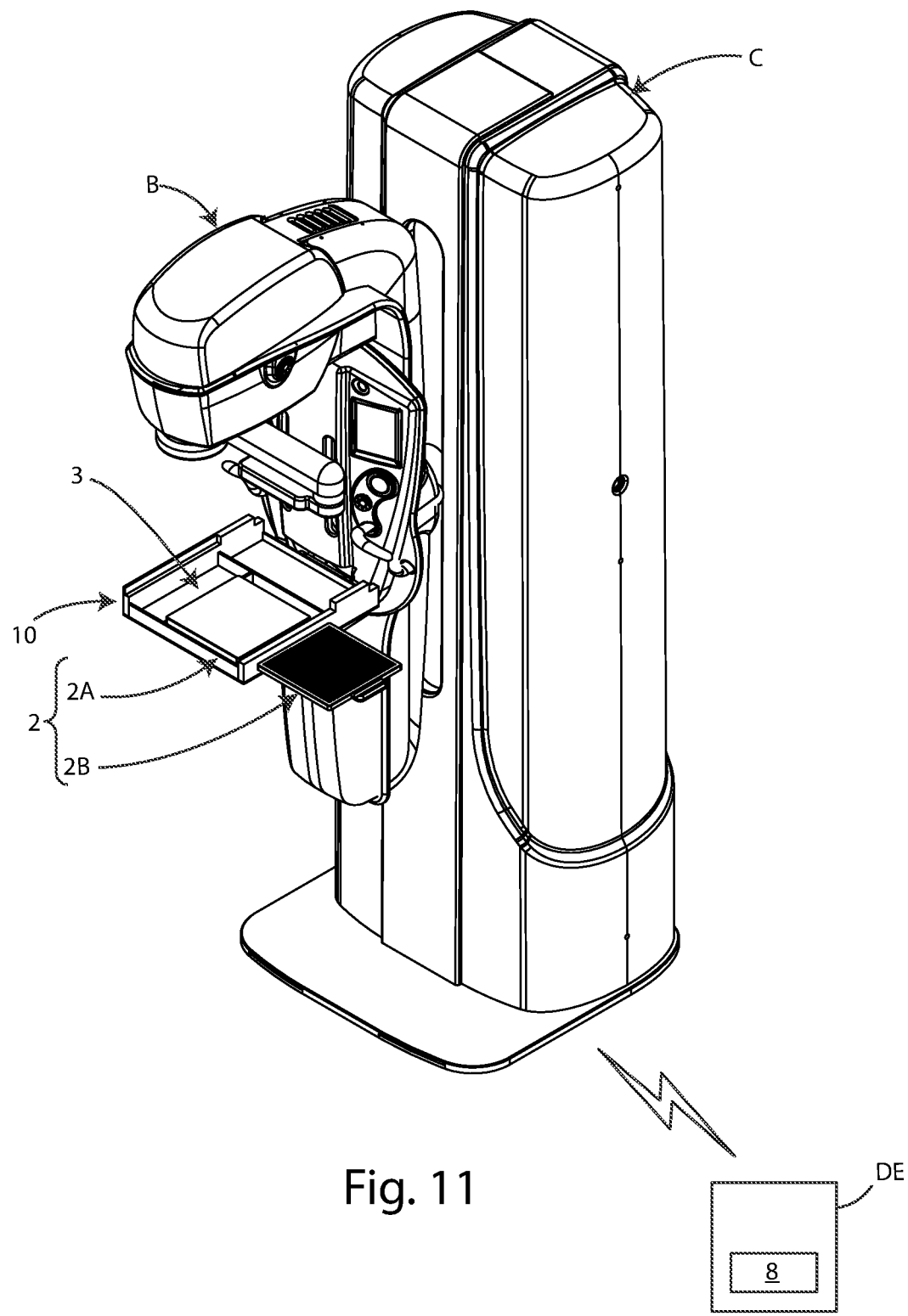
FIG. 11 shows the variant of the multimodal system of FIG. 9, wherein the scintigraphic collimator has been uncoupled from the gamma ray detector.

FIG. 11 shows the multimodal system when the scintigraphic collimator 2B is uncoupled and extracted from the gamma ray detector 2A.

Figure 12:
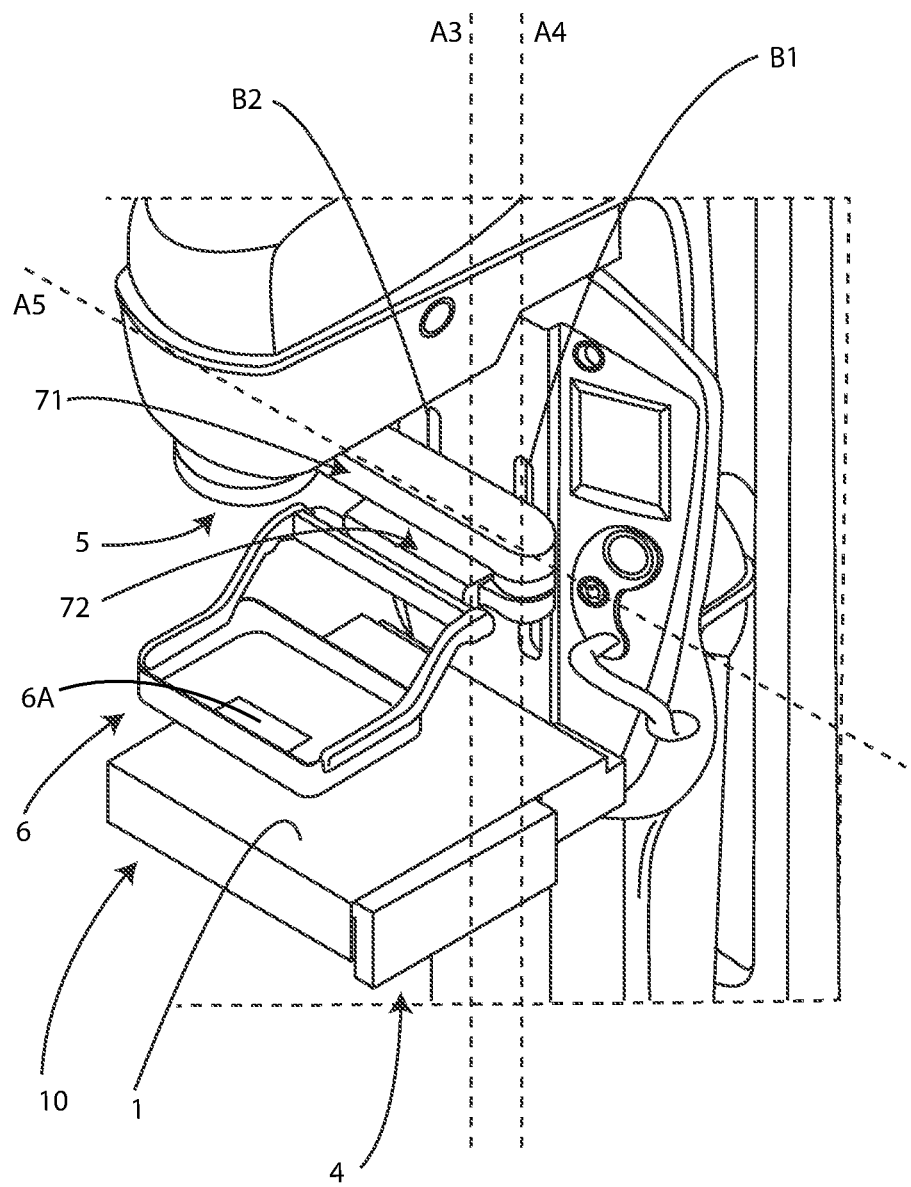
FIG. 12 shows a part of a further variant of the multimodal system, wherein said multimodal system is provided with a compressor connected to a second gamma camera, the latte being in turn connected to the arm of the multimodal system.

According to the invention, as shown in FIG. 12, said multimodal system comprises a second gamma camera 5 and a compressor 6 to compress the breast.

Furthermore, said second gamma camera 5 is connected to the first element of supporting and connecting means (disclosed below) in such a way as to rotate in the space around a point.

In particular, said second gamma camera 5 is connected to said first element 71 by means of a spherical joint, not shown.

Furthermore, said second gamma camera 5 is connected to the arm B of the multimodal system in such a way as to movable along a third axis A3, perpendicular to the supporting plane 1.

In other words, in addition to rotating in the space, the second gamma camera 5 is adapted to slide along said third axis A3 toward a first direction or toward a second direction, opposite to said first direction.

Said second gamma camera 5 is connected to the arm B of the multimodal system through supporting and connecting means for supporting said second gamma camera and connecting to the arm B and said arm B is provided with second guiding means for the sliding of said supporting and connecting means.

In the embodiment being disclosed, said second guiding means comprise a first eyelet B1 and a second eyelet B2, spaced from said first eyelet B1, and said supporting and connecting means comprise:

a first element 71, connecting to said second gamma camera 5, and a second element 72, connected to said first element 71 and connected to the arm B in such a way as to slide along said third axis A3, through said second guiding means.

With particular reference to the first element 71, said first element 71 is connected rotatably to said second element 72 in such a way as to rotate around a fourth axis A4, perpendicular to said supporting plane 1.

In other words, said first element 71 rotates with respect to said second element 72 on a further plane, parallel to the supporting plane.

Figure 13:
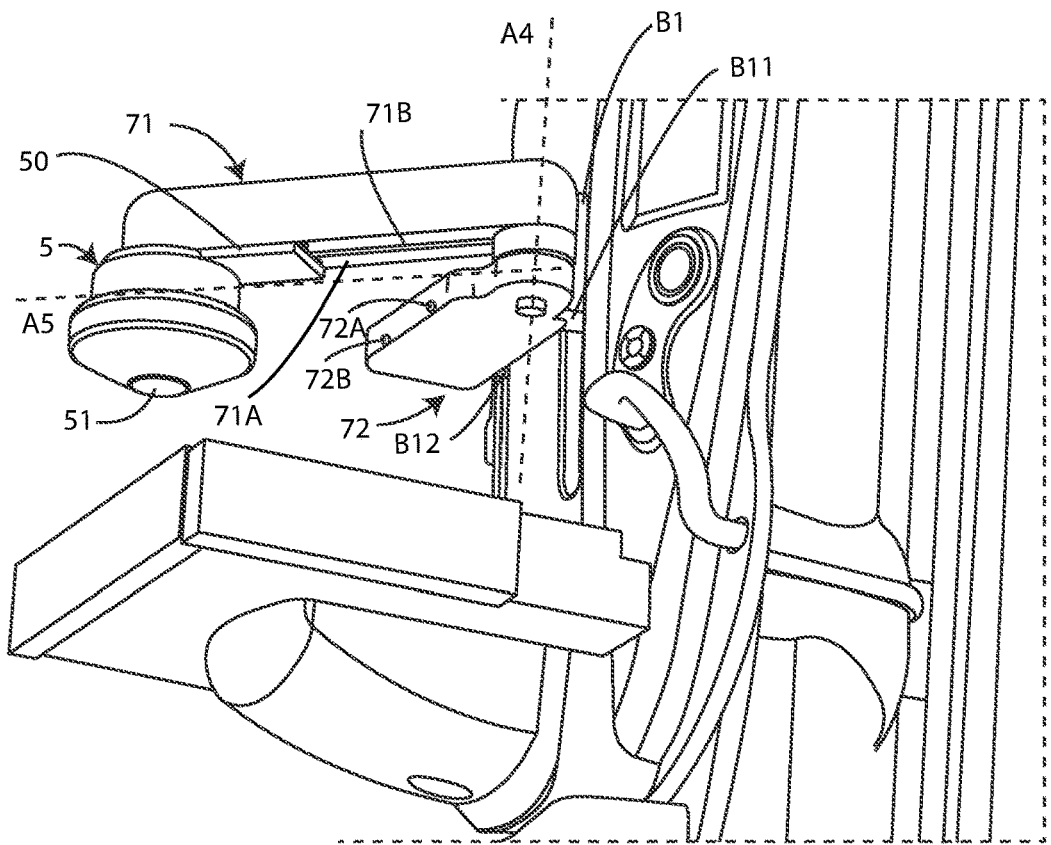
FIG. 13 shows a detail of the multimodal system of FIG. 12 concerning the second gamma camera and to the supporting and connecting means for supporting and connecting said second gamma camera to the arm of the multimodal system.

Furthermore, as it can be seen from the FIG. 13, said first element 71 comprise a first surface 71A and said second gamma camera 5 is sliding on said first surface 71A along a fifth axis A5, perpendicular to said third axis A3.

To this end, said first surface 71A is provided of third guiding means to allow the sliding of the second gamma camera 5 along said first surface 71A.

In the embodiment being disclosed, said third guiding means comprise a C-shaped guiding element indicated with the reference 71B.

A supporting element 50 connected to said second gamma camera 5 is configured to slide on said third guiding means.

Figure 14:
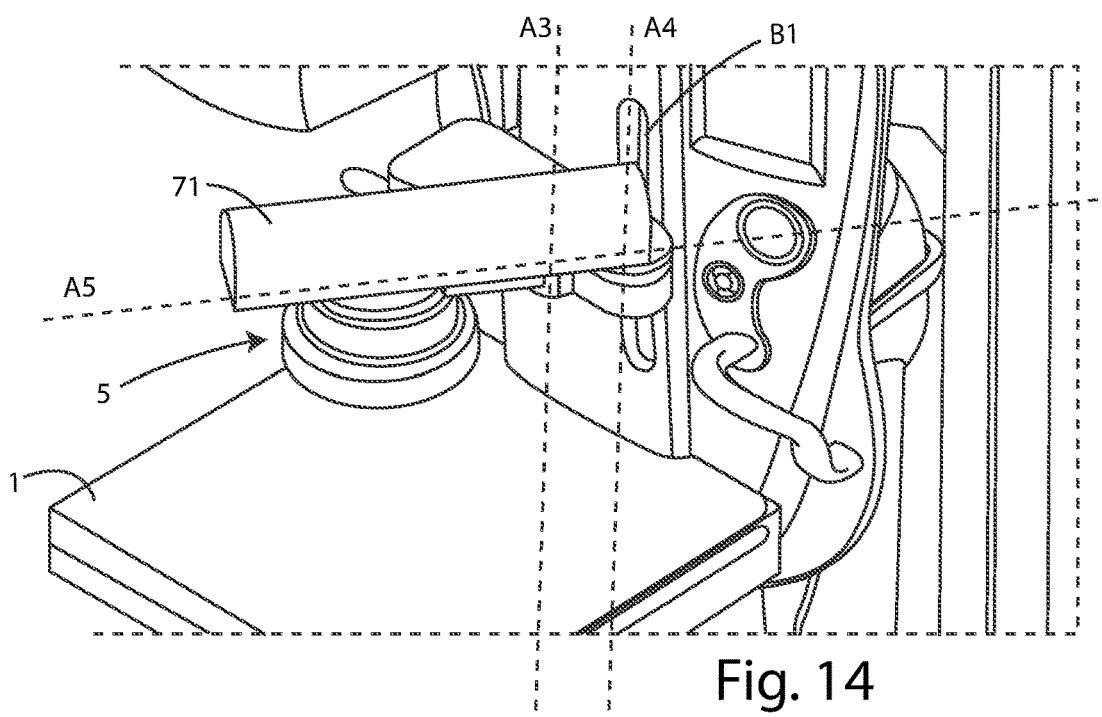
FIG. 14 shows the second gamma camera range in a position different from that shown in FIG. 13.

FIG. 14 shows the second gamma camera 5 when it is translated on said third guiding means.

With particular reference to the second element 72, said second element 72 is provided of coupling means to allow the compressor 6 to be coupled with said second element 72 in removable manner and of further coupling means to allow the compressor 6 to be coupled to the arm B of the multimodal system.

In the embodiment being disclosed, said coupling means comprise a first hole 72A and a second hole 72B for inserting a respective protruding portion of the compressor 6 (FIG. 13).

Said further coupling means comprise a third hole (not shown) for receiving a first pin B11 of the arm B and a fourth hole (not shown) for receiving a second pin B12 of the arm B, where each pin slides in a respective eyelet B1 and B2.

Said compressor 6 is provided o fan opening 6A to allow the second gamma camera 5 to contact a breast portion at the opening 6A in order to compress said breast portion.

Hence, the second gamma camera 5 plays also a compression function with respect a specific breast portion.

Said second gamma camera 5 has a substantially truncated conical shape and a surface 51 of reduced dimensions to contact said specific portion.

The rotation of the second gamma camera 5 in the space can be manual or motorized.

In the case in which said rotation is motorized, the second gamma camera 5 comprises inside rotating means for rotating the second gamma camera range 5 in the space, around the spherical joint which connects said second gamma camera to said first element 71, and said control logic unit 8 is connected to said rotating means and configured to rotate said rotating means of a predetermined angle.

Said rotating means can comprise, for example, a first oscillating actuator and a second oscillating actuator, arranged on axes perpendicular to each other.

In the embodiment being described, said rotating means are motorized. However, said rotating means may be manual, without thereby departing from the invention.

The movement of the second gamma camera 5 along said first surface 71A and the rotary motion of the first element 71 with respect to the second element 72 can be manual or motorized.

In the event that said movements are motorized, said first element 71 comprises third moving means (for example at least one motor) for moving said second gamma camera 5 along said first surface 71A, said second element 72 comprises fourth moving means (e.g. at least one further motor) for rotating said first element 71 with respect to said second element 72.

Said logic control unit 8 is connected to said third moving means and to said fourth moving means and is configured to send to said third moving means and to said fourth moving means a position signal for the second gamma camera 5, where said position signal contains the spatial coordinates associated with the position to be reached by said second camera range 5.

Accordingly, the second gamma camera 5 can translate along the first surface 71A of the first element 71 of a predetermined distance and/or rotate on said further plane, parallel to the supporting plane, by rotating said first element 71.

For example, said spatial coordinates can be obtained through a biopsy system and provided to the control logic unit 8.

However, the control logic unit 8 can also be configured to store the spatial coordinates associated with the second gamma camera 5 and send them to a biopsy system, to which it is connected.

With reference to the position of the motors, said first motor and said further motor can be arranged elsewhere in the multimodal system, without thereby departing from the scope of the invention.

In the embodiment being disclosed, said third moving means are motorized. However, said first moving means can be manual, without thereby departing from the invention.

Advantageously, as already said, the multimodal system, object of the invention, allows to obtain an X-ray image of the breast, without the need to resort to one or more further processing on the pre-processing images and/or on the post-processing images. This is due to the fact that, when the X-ray detector is in use, said X-ray detector is in contact or substantially in contact with the supporting plane for the breast. As a result, the distance between the X-ray detector and the breast supporting plane is zero or extremely reduced.

A second advantage is given by the fact that the multimodal system, object of the invention, is devoid of mechanisms for moving the X-ray detector, so that the structure of the detection module is simplified.

A further advantage is given by the fact that a single compartment, arranged between the breast supporting plane and a gamma ray detector, is adapted to receive one at a time both the X-ray detector and the scintigraphic collimator (which forms a first gamma camera with said gamma ray detector) to respectively obtain an X-ray image and a molecular image, depending on the device inserted in the compartment. Hence, it is not necessary to provide a first compartment for the X-ray detector and a second compartment for the scintigraphic collimator, but both the X-ray detector and the scintigraphic collimator are inserted in turn in the same compartment. Accordingly, the distance between the X-ray detector and the supporting plane is equal to the distance between the gamma camera and the supporting plane.

The present invention has been described for illustrative, but not limitative purposes, according to its preferred embodiment, but it is to be understood that variations and/or modifications can be carried out by a skilled in the art, without departing from the scope thereof, as defined according to enclosed claims.

The invention claimed is:

1. A multimodal system for obtaining senological images by means of X-ray and MBI techniques, comprising:
   a supporting plane (1) for the breast,
   a gamma ray detector (2A) for obtaining at least a molecular image,
   a detection module (10) comprising inside said gamma ray detector (2A), wherein said gamma ray detector (2A) is arranged on a first plane, parallel to said supporting plane, and further comprising:
      one of a X-ray detector (4) for obtaining at least an X-ray image and a scintigraphic collimator (2B); said scintigraphic collimator (2B), when in use, being coupled with said gamma ray detector (2A) and forming with said gamma ray detector (2A) a first gamma camera (2); and
      a compartment (3) configured for receiving one at time said X-ray detector (4) or said scintigraphic collimator (2B), wherein said compartment (3) is arranged between said supporting plane (1) and said gamma ray detector (2A) on a second plane, parallel to said supporting plane (1), different from said first plane, and wherein said compartment (3) comprises first guiding means (3A, 3B) for inserting said X-ray detector (4) or said scintigraphic collimator (2B),
   wherein said detection module (10) being configured to allow the extraction of said X-ray detector (4) from the detection module (10) to insert said scintigraphic collimator (2B) or the extraction of said scintigraphic collimator (2B) to insert said X-ray detector (10).

2. The multimodal system according to claim 1, characterized in that said first guiding means (3A, 3B) comprise a first guiding element (3A), arranged on a first side of said compartment (3), and a second guiding element (3B), arranged on a second side of said compartment (3), opposite said first side.

3. The multimodal system according to claim 1, characterized in that
   said detection module (10) comprises said supporting plane (1) and said supporting plane (1) is a first surface of said detection module (10), or
   said supporting plane (1) is coupled with a first surface of said detection module (10) in a removable manner.

4. The multimodal system according to claim 3, characterized in that X-ray detector (4) comprises inside an anti-diffusion grid (40C).

5. The multimodal system according to claim 4, characterized in that said X-ray detector (4) comprises first moving means for moving said anti-diffusion grid (40C) along an axis lying on a third plane parallel to said supporting plane (1); said first moving means being manual or motorized.

6. The multimodal system according to claim 1, characterized in that said gamma ray detector (2A) is arranged in a fixed position or movable on said first plane.

7. The multimodal system according to claim 1, characterized in that
said gamma ray detector (2A) and said scintigraphic collimator (2B) have dimensions equal to each other and smaller to the dimensions of said compartment (3), in that
said first gamma camera (2) is movable on said first plane.

8. The multimodal system according to claim 7, characterized in that said first gamma camera (2) is configured to translate along a first axis (A1), and along a second axis (A2), perpendicular to said first axis (A1), wherein said first axis (A1) and said second axis (A2) lie on said first plane.

9. The multimodal system according to claim 8, characterized in that said detection module (10) comprises inside second moving means for moving said first gamma camera (2) along said first axis (A1) and said second axis (A2), wherein said second moving means are connected to said gamma ray detector (2A); said second moving means being manual or motorized.

10. The multimodal system according to claim 1, characterized in that said multimodal system comprises:
a body (C),
an arm (B) connected to said body (C) in such a way as to rotate with respect to said body (C) of a predetermined angle, and
a second gamma camera (5),
supporting and connecting means (71, 72) for supporting said second gamma camera (5) and connecting said second gamma camera (5) to said arm (B) so that said second gamma camera (5) is movable along a third axis (A3), perpendicular to said support plane (1), said supporting and connecting means (71, 72) comprising:
a first element (71), connected to said second camera chamber (5), and
a second element (72) connected to said first element (71) and to said arm (B) so as to slide along said third axis (A3),
wherein
said first element (71) is rotatably connected to said second element (72) so as to rotate about a fourth axis (A4) perpendicular to said support plane (1), and
said second gamma camera (5) is connected to said first element (71) so as to rotate in the space around a point.

11. The multimodal system according to claim 10, characterized in that said second gamma camera (5) is connected to said first element (71) by means of a spherical joint.

12. The multimodal system according to claim 11, characterized in that said second gamma camera (5) comprises rotating means for rotating said second gamma camera (5) around said spherical joint; said rotating means being manual or motorized.

13. The multimodal system according to claim 10, characterized in that said first element (71) comprises a first surface (71A) and said second gamma camera (5) slides on said first surface (71A) along a fifth axis (A5), perpendicular to said third axis (A3).

14. The multimodal system according to claim 13, characterized in that said first surface (71A) is provided with third guiding means (71B) to allow the sliding of the second gamma camera (5) along said first surface (71A).

15. The multimodal system according to claim 13, characterized in that said multimodal system comprises third moving means for moving said second gamma camera (5) along said first surface (71A), wherein said third moving means are manual or motorized, and fourth moving means for rotating said first element (71) with respect to said second element (72), and wherein said fourth moving means are manual or motorized.

16. The multimodal system according to claim 10, characterized in that said multimodal system comprises a compressor (6), coupable to said second element (72), said compressor (6) being provided with an opening (6A) to allow said second gamma camera (5) to contact a breast portion at said opening (6A),
in that said second element (72) is provided with coupling means (72A, 72B) to allow said compressor (6) to be coupled with said second element (72) in a removable manner.

* * * * *